United States Patent [19]

Brana et al.

[11] 4,204,063

[45] May 20, 1980

[54] N(AMINOALKYL)-NAPHTHALIMIDES AND THEIR DERIVATIVES

[75] Inventors: Miguel F. Brana; Antonio M. Sanz; Rafael P. Alvarez-Ossorio; Cristobal M. Roldan; Cristina R. Fernandez de Gamboa, all of Madrid, Spain

[73] Assignee: Laboratorios Made, S.A., Madrid, Spain

[21] Appl. No.: 911,801

[22] Filed: Jun. 2, 1978

[30] Foreign Application Priority Data

Jun. 4, 1977 [ES] Spain ................................ 459497

[51] Int. Cl.$^2$ ................... C07D 401/06; C07D 413/06
[52] U.S. Cl. ........................................ 546/99; 546/100; 544/126; 544/361; 424/248.54; 424/250; 424/258
[58] Field of Search ........ 260/281 N, 281 NH, 281 S; 546/99, 100; 544/126

[56] References Cited

U.S. PATENT DOCUMENTS

| | | | |
|---|---|---|---|
| 1,796,012 | 3/1931 | Eckert | 260/281 S |
| 1,886,797 | 11/1932 | Eckert | 260/281 S |
| 3,308,127 | 3/1967 | Senshu | 260/281 S |
| 3,310,564 | 3/1967 | Kasai | 260/281 N |
| 3,330,834 | 7/1967 | Senshu | 260/281 N |
| 3,362,958 | 1/1968 | Schellhammer | 260/281 N |
| 3,625,947 | 12/1971 | Noguchi et al. | 260/281 NH |
| 3,798,224 | 3/1974 | Hotta | 260/281 NH |
| 4,077,960 | 3/1978 | Shimada | 260/281 NH |

FOREIGN PATENT DOCUMENTS

| | | | |
|---|---|---|---|
| 530906 | 8/1931 | Fed. Rep. of Germany | 260/281 N |
| 2423548 | 11/1975 | Fed. Rep. of Germany | 260/281 N |
| 2423547 | 12/1975 | Fed. Rep. of Germany | 260/281 N |
| 1344883 | 10/1963 | France | 260/281 N |
| 51/137724 | 11/1976 | Japan . | |
| 309552 | 6/1930 | United Kingdom | 260/281 N |

OTHER PUBLICATIONS

Imahori et al., Chem. Abs. 79, 54820h (1973).
Kadhim et al., Chem. Abs. 81, 154514e (1974).
Laboratorios Mad SA, Chem. Abs. 86, 89639m (1976).
Laboratorios Made SA, Chem. Abs. 83, 97061 (1975).
Dreyfus et al., Bull. Chem. Soc., France, 1975, 1196–1200.

Primary Examiner—Mark L. Berch
Attorney, Agent, or Firm—Blanchard, Flynn, Thiel, Boutell & Tanis

[57] ABSTRACT

N-substituted-3-substituted naphthalimides are prepared by reacting 3-substituted naphthalic acid with a compound having a primary amino group. The naphthalimides possess cytotoxic properties.

5 Claims, No Drawings

N(AMINOALKYL)-NAPHTHALIMIDES AND THEIR DERIVATIVES

CROSS-REFERENCE TO RELATED APPLICATION

This application is related to Ser. No. 834,299, filed Sept. 17, 1977, now U.S. Pat. No. 4,146,720.

BACKGROUND OF THE INVENTION

Field of the Invention

This invention relates to substituted naphthalimides and derivatives thereof, such as the salts thereof with pharmacologically acceptable acids, N-oxides and quaternary ammonium salts, etc., which have great biological interest as anti-tumor agents.

These compounds have the general formula

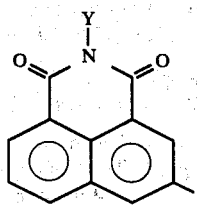

wherein X is alkyl, hydroxyl, alkoxy, halogen, amino, sulphonic acid, nitro, $NHCOOC_2H_5$, acetylamino or acetoxy, and Y is a valence bond or alkylene having one to three carbons and bonded to a nitrogen-containing group, such as dimethylamino, diethylamino, pyrrolidino, piperidino, N-methylpiperazino, morpholino or ureyl, with the proviso that when X is nitro, Y is not 2-dimethylaminoethyl, 2-diethylaminoethyl, 2-(N-pyrrolidino)ethyl or 2-(N-piperidino)ethyl.

The general methods of synthesis of these compounds is based on the reaction of an active derivative of the "X" substituted naphthalic acid with the corresponding primary amine, in a suitable solvent, at temperatures in the range of from the freezing point to the boiling point of the solvent, wherein ambient temperature is effective in the majority of cases. Once the reaction is completed, the resulting product is filtered and crystallized in an appropriate solvent.

The naphthalimides of the type shown in the formula above act as ADN and ARN-inhibiting agents and are useful as cytostatic agents.

The following are some non-limiting examples of the scope of this invention.

The elemental analyses of the described compounds are within ±0.4% in accordance with international standards.

Example 1 ($X=NO_2$; $Y=CH_2-CH_2-CH_2-N(CH_3)_2$)

Into an Erlenmeyer flask of 100 ml capacity, provided with an electromagnetic stirrer, there is placed 2.43 g (0.01 mols) of 3-nitro-1,8-naphthalic acid anhydride and 20 ml of ethanol, and then there is added 1.02 g (0.01 mols) of 3-dimethylaminopropylamine. The mixture is stirred for two hours and the solid thus formed is filtered and recrystallized from ethanol, obtaining 2.75 g (84% yield).

The N-(3-dimethylaminopropyl)-3-nitro-1,8-naphthalimide is a yellow solid having a melting point of 99° C.

Example 2 ($X=NO_2$; $Y=CH_2-CH_2-CH_2-N(CH_2-CH_3)_2$)

The same process is used as in Example 1, except that there is used 1.30 g of 3-diethylaminopropylamine and there is obtained 3.1 g (89% yield) of N-(3-diethylaminopropyl)-3-nitro-1,8-naphthalimide having a melting point of 105° C. (ethanol).

Example 3

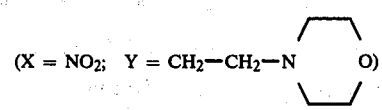

The same process is used as in Example 1, except that there is used 1.30 g (0.01 mols) of N-(2-aminoethyl)-morpholine, and there is obtained 2.35 g (68% yield) of N-2-(N-morpholino)-ethyl-3-nitro-1,8-naphthalimide having a melting point of 189°-90° C. (DMF/water).

Example 4

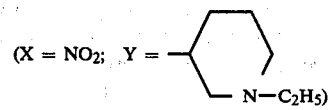

The same process is used as in Example 1, except that there is used 1.28 g (0.01 mols) of 1-ethyl-3-aminopiperidine, and there is obtained 1.31 g (37% yield) of N-3-(1-ethylpiperidino)-3-nitro-1,8-naphthalimide having a melting point of 157°-58° C. (DMF/water).

Example 5

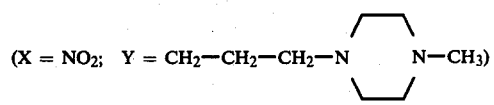

The same process is used as in Example 1, except that there is used 1.57 g (0.01 mols) of 1-(3-aminopropyl)-4-methylpiperazine, and there is obtained 2.80 g (74.8% yield) of N-3-(4-methyl-1-piperazino)-propyl-3-nitro-1,8-naphthalimide having a melting point of 154°-55° C. (ethanol/water).

Example 6 ($X=NO_2$; $Y=N(CH_3)_2$)

Into a flask of 100 ml capacity, provided with a magnetic stirrer and a reflux port, there are added 2.43 g (0.01 mols) of 3-nitro-1,8-naphthalic acid anhydride, 0.48 g (0.01 mols) of N,N-dimethylhydrazine and 50 ml of ethanol, and the contents are heated under reflux with stirring for 10 hours. At the end of this time a brown solid is precipitated which is recrystallized from ethanol, thereby obtaining 2.0 g (70.2% yield) of N-dimethylamino-3-nitro-1,8-naphthalimide having a melting point of 233°-34° C.

Example 7

(X = NO₂; Y = N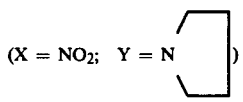)

The same process is used as in the preceding Example 6, except that there is used 0.2 g (0.0023 mols) of N-aminopyrrolidine, and there is obtained 0.25 g (40% yield) of N-(1-pyrrolidino)-3-nitro-1,8-naphthalimide having a melting point of 227°-28° C. (DMF/water).

Example 8 (X=NO₂; Y=NHCONH₂)

The same process is used as in Example 6, except that there is used 0.75 g of semicarbazide, and there is obtained 2.7 g (90% yield) of N-ureyl-3-nitro-1,8-naphthalimide having a melting point of above 300° C. (DMF).

Example 9 (X=NH₂; Y=CH₂—CH₂—N(CH₃)₂)

Into an Erlenmeyer flask of 100 ml capacity provided with an electromagnetic stirrer, there are placed 1.06 g (0.005 mols) of 3-amino-1,8-naphthalic anhydride, 0.44 g (0.005 mols) of 2-dimethylamino-ethylamine and 50 ml of ethanol. The mixture is stirred for eight hours and the solid formed is filtered and recrystallized from chloroform-n-hexane, and there is obtained 1.33 g (82.3% yield) of yellow needles of a melting point of 175°-77° C.

Example 10 (X=NH₂; Y=CH₂—CH₂—N(CH₂—CH₃)₂)

The same process is used as in Example 9, except that there is used 0.58 g (0.005 mols) of 2-diethylaminoethylamine, and there is obtained 1.22 g (83.5% yield) of N-(2-diethylaminoethyl)-3-amino-1,8-naphthalimide having a melting point of 120°-22° C. (ethanol/water).

Example 11

(X = NH₂; Y = CH₂—CH₂—N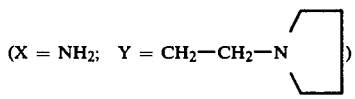)

The same process is used as in Example 9, except that there is used 0.57 g (0.005 mols) of N-(2-aminoethyl)-pyrrolidine, and there is obtained 1.14 g (78.6% yield) of N-[2-(1-pyrrolidino)-ethyl]-3-amino-1,8-naphthalimide having a melting point of 197°-199° C. (ethanol).

Example 12

(X = NH₂; Y = CH₂—CH₂—N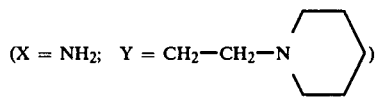)

The same process is used as in Example 9, except that there is used 0.64 g (0.005 mols) of N-(2-aminoethyl)-piperidine, and there is obtained 1.20 g (74.5% yield) of N-[2-(1-piperidino)-ethyl]-3-amino-1,8-naphthalimide having a melting point of 185°-86° C. (DMF/water).

Example 13

(X = NH₂; Y = CH₂—CH₂—N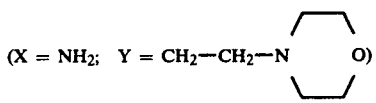O)

The same process is used as in Example 9, except that there is used 0.85 g (0.0065 mols) of N-(2-aminoethyl)-morpholine, and there is obtained 1.6 g (76.2% yield) of N-[2-(1-morpholino)-ethyl]-3-amino-1,8-naphthalimide having a melting point of 236°-38° C. (ethanol).

Example 14 (X=NH₂; Y=CH₂—CH₂—CH₂—N(CH₃)₂)

The same process is used as in Example 9, except that there is used 0.51 g (0.005 mols) of 3-dimethylaminopropylamine, and there is obtained 1.3 g (91% yield) of N-(3-dimethylaminopropyl)-3-amino-1,8-naphthalimide having a melting point of 81°-83° C. (ethanol-water).

Example 15 (X=NH₂; Y=CH₂—CH₂—CH₂—N(CH₂—CH₃)₂)

The same process is used as in Example 9, except that there is used 0.65 g (0.005 mols) of 3-diethylaminopropylamine, and there is obtained 1.3 g (80.3% yield) of N-(3-diethylaminopropyl)-3-amino-1,8-naphthalimide having a melting point of 139°-40° C. (chloroform/n-hexane).

Example 16

(X = NH₂; Y = CH₂—CH₂—CH₂—N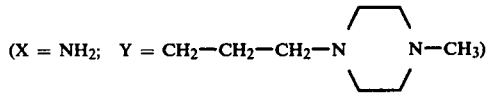N—CH₃)

The same process is used as in Example 9, except that there is used 0.79 g (0.005 mols) of N-(3-aminopropyl)-N-methylpiperazine, and there is obtained 1.3 g (74% yield) of N-[3-(4-methyl-1-piperazino)-propyl]-3-amino-1,8-naphthalimide having a melting point of 153°-54° C. (chloroform/n-pentane).

Example 17

(X=NH₂; Y = N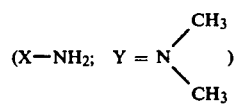)

The same process is used as in Example 6, except that there are used 1.06 g (0.05 mols) of 3-amino-1,8-naphthalic acid anhydride and 0.48 g (0.01 mols) of N,N-dimethylhydrazine, and there is obtained 0.64 g (50.1% yield) of N-dimethylamino-3-amino-1,8-naphthalimide having a melting point of 220°-22° C. (DMF/water).

Example 18 (X=Cl; Y=CH₂—CH₂—N(CH₃)₂)

Into a flask of 100 ml capacity provided with a magnetic stirrer and port for reflux there are placed 0.67 g (0.003 mols) of 3-chloro-1,8-naphthalic acid anhydride and 0.26 g (0.03 mols) of 2-dimethylaminoethylamine and 30 ml of ethanol. The mixture is stirred for three hours at 80° C. (water bath). The solvent is removed by vacuum and the residue is recrystallized in an acetone-water mixture, and there is obtained 0.15 g (20% yield)

of N-(2-dimethylaminoethyl)-3-chloro-1,8-naphthalimide having a melting point of 161°–63° C.

Example 19

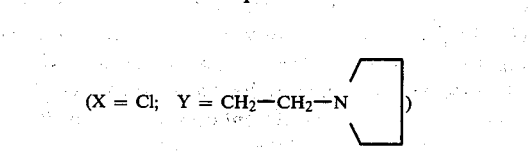

The same process is used as in Example 9, except that there are used 1.16 g (0.005 mols) of 3-chloro-1,8-naphthalic acid anhydride and 0.57 g (0.005 mols) of 2-(N-pyrrolidino)-ethylamine, and there is obtained 0.4 g (20% yield) of N-[2-(1-pyrrolidino)-ethyl]-3-chloro-1,8-naphthalimide having a melting point of 173°–74° C. (acetone/water).

Example 20

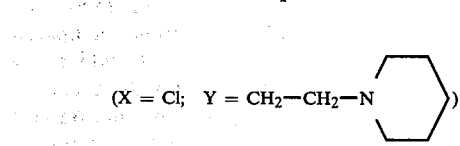

The same process is used as in Example 9, except that there are used 1.16 g (0.005 mols) of 3-chloro-1,8-naphthalic acie anhydride and 0.64 g (0.005 mols) of 2-(N-piperidino)ethylamine, and there is obtained 0.35 g (20% yield) of N-[2-(1-piperidino)-ethyl]-3-chloro-1,8-naphthalimide having a melting point of 137°–38° C. (acetone/water).

Example 21

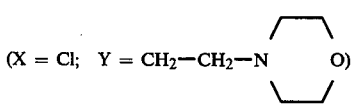

The same process is used as in Example 9, except that there are used 1.16 g (0.005 mols) of 3-chloro-1,8-naphthalic acid anhydride and 0.64 g (0.005 mols) of 2-(N-morpholino)ethylamine, and there is obtained 1.07 g (67% yield) of N-[2-(1-morpholino)-ethyl]-3-chloro-1,8-naphthalimide having a melting point of 150°–52° C. (acetone/water).

Example 22 (X=Cl; Y=CH$_2$—CH$_2$—CH$_2$—N(CH$_3$)$_2$)

The same process is used as in Example 9, except that there are used 1.16 g (0.005 mols) of 3-chloro-1,8-naphthalic acid anhydride and 0.51 g (0.005 mols) of 3-dimethylaminopropylamine, and there is obtained 0.3 g (25% yield) of N-(3-dimethylaminopropyl)-3-chloro-1,8-naphthalimide having a melting point of 75°–76° C. (acetone/water).

Example 23 (X=OH; Y=CH$_2$—CH$_2$—N(CH$_3$)$_2$)

The same process is used as in Example 9, except that there are used 1.07 g (0.005 mols) of 3-hydroxy-1,8-naphthalic acid anhydride and 0.44 g (0.005 mols) of 2-dimethylaminoethylamine, and there is obtained 0.88 g (62% yield) of N-(2-dimethylaminoethyl)-3-hydroxy-1,8-naphthalimide having a melting point of 213°–15° C. (DMF/water).

Example 24

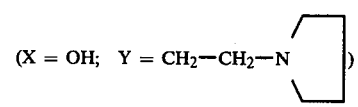

The same process is used as in Example 9, except that there are used 1.07 g (0.005 mols) of 3-hydroxy-1,8-naphthalic acid anhydride and 0.57 g (0.005 mols) of N-(2-aminoethyl)pyrrolidine, and there is obtained 1.3 g (81% yield) of N-[2-(1-pyrrolidino)-ethyl]-3-hydroxy-1,8-naphthalimide having a melting point of 212°–13° C. (water/DMF).

Example 25

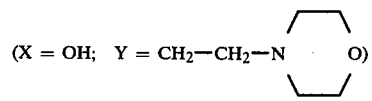

The same process is used as in Example 9, except that there are used 1.48 g (0.007 mols) of 3-hydroxy-1,8-naphthalic acid anhydride and 0.91 g (0.007 mols) of 2-(N-morpholino)ethylamine, and there is obtained 0.63 g (27.3% yield) of N-[2-(1-morpholino)-ethyl]-3-hydroxy-1,8-naphthalimide having a melting point of 200°–202° C. (DMF/water).

Example 26 (X=OCH$_3$; Y=CH$_2$—CH$_2$—N(CH$_3$)$_2$)

The same process is used as in Example 9, except that there are used 0.62 g (0.003 mols) of 3-methoxy-1,8-naphthalic acid anhydride and 0.26 g (0.003 mols) of 2-dimethylaminoethylamine, and there is obtained 0.6 g. (68.2% yield) of N-(2-dimethylaminoethyl)-3-methoxy-1,8-naphthalimide having a melting point of 112°–114° C. (ethanol/water).

Example 27

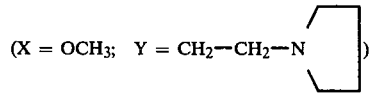

The same process is used as in Example 9, except that there are used 0.51 g (0.0023 mols) of 3-methoxy-1,8-naphthalic acid anhydride and 0.26 g. (0.0023 mols) of N-(2-aminoethyl)pyrrolidine, and there is obtained 0.2 g (28.6% yield) of N-[2-(1-pyrrolidino)-ethyl]-3-methoxy-1,8-naphthalimide having a melting point of 119°–20° C. (ethanol/water).

Example 28 (X=NHCOOC$_2$H$_5$; Y=CH$_2$—CH$_2$—N—(CH$_3$)$_2$)

The same process is used as in Example 9, except that there are used 0.7 g (0.0025 mols) of 3-ethoxycarbonylamino-1,8-naphthalic acid anhydride and 0.22 g (0.0025 mols) of 2-dimethylaminoethylamine, and there is obtained 0.51 g (57.3% yield) of N-(dimethylaminoethyl)-3-ethoxycarbonylamino-1,8-naphthalimide having a melting point of 197°–98° C. (acetone/water).

Example 29

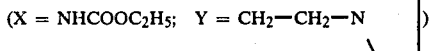

The same process is used as in Example 9, except that there are used 0.7 g (0.0025 mols) of 3-ethoxycarbonylamino-1,8-naphthalic acid anhydride and 0.28 g (0.0025 mols) of N-(2-aminoethylpyrrolidine, and there is obtained 0.7 g (77.8% yield) of N-[2-(1-pyrrolidino)-ethyl]-3-ethoxycarbonylamino-1,8-naphthalimide having a melting point of 188°–89° C. (ethanol).

Example 30 (X=NHCOCH₃; Y=CH₂—CH₂—N(CH₃)₂)

The same process is used as in Example 9, except that there are used 2.55 g (0.01 mols) of 3-acetylamino-1,8-naphthalic acid anhydride and 0.88 g (0.01 mols) of 2-dimethylaminoethylamine, and there is obtained 2.7 g (83% yield) of N-(2-dimethylaminoethyl)-3-acetylamino-1,8-naphthalimide having a melting point of 221°–23° C. (ethanol/water).

Example 31

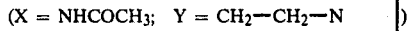

The same process is used as in Example 9, except that there are used 0.85 g (0.0033 mols) of 3-acetylamino-1,8-naphthalic acid anhydride and 0.40 g (0.0033 mols) of N-(2-aminoethyl)-pyrrolidine, and there is obtained 1.1 g (95% yield) of N-[2-(1-pyrrolidino)-ethyl]-3-acetylamino-1,8-naphthalimide having a melting point of 221°–22° C. (ethanol/water).

Example 32

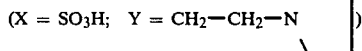

The same process is used as in Example 9, except that there are used 1.0 g (0.003 mols) of 3-sulfonaphthalic acid anhydride and 0.26 g (0.003 mols) of 2-dimethylaminoethylamine, and there is obtained 0.1 g (10% yield) of N-[2-(1-pyrrolidino)ethyl]-3-sulfo-1,8-naphthalimide having a melting point of more than 300° C. (water).

Example 33 (X=C(CH₃)₃; Y=CH₂—CH₂—N(CH₃)₂)

The same process is used as in Example 9, except that there are used 0.15 g (0.0006 mols) of 3-tert-butyl-1,8-naphthalic acid anhydride and 0.05 g (0.0006 mols) of 2-dimethylaminoethylamine, and there is obtained 0.16 g (84% yield) of N-(2-dimethylaminoethyl)-3-tert-butyl-1,8-naphthalimide having a melting point of 123°–24° C. (ethanol/water).

As has been indicated, the most important biological activity in this series of compounds is its anti-neoplastic action. To determine this, "screening" tests have been made of the cytotoxic activity of the compounds on the so-called He-La cells, cultivated in a monolayer on glass bottles.

Testing commences using a culture having approximately 125,000 cells per milliliter. They are dispersed with trypsin and are maintained in suspension by stirring until the moment they are placed in tubes. After the cells have become stuck to the wall of the tubes, the test compound is added in different concentrations. In addition to blank control tubes (no test compound was added), controls are used to which the compound 6-mercaptopurine is added. The inhibitory dose 50 ($ID_{50}$) of 6-mercaptopurine is known, that is, the dose which inhibits cellular growth by 50%.

After 72 hours the results are read.

First an optical reading is made under a microscope, which gives an idea of the amounts of the cells which have been affected by the test compounds. Then the proteins are determined (Lowry method modified by Dyama and Eagle: Proc. Soc. Exper. Biol. Med. 305, 1956) in each culture tube and the results are compared with those obtained in the control tubes, to which test compounds have not been added. With these data, a graph is made in which the concentrations (micrograms per ml) of the compound are represented in relation to the percentage of inhibition of cellular growth, thereby obtaining the $ID_{50}$.

The data obtained as to the measure of $ID_{50}$ are given in the following table, in which X and Y have the significance indicated previously.

| Ex. | X | Y | $ID_{50}$ |
|---|---|---|---|
| 1 | $NO_2$ | $CH_2—CH_2—CH_2—N(CH_3)_2$ | 1 |
| 2 | $NO_2$ | $CH_2—CH_2—CH_2—N(CH_2—CH_3)_2$ | 5 |
| 3 | $NO_2$ | $CH_2—CH_2—N\underset{\diagdown\_\_\diagup}{\overset{\diagup\phantom{XX}\diagdown}{\phantom{XX}}}O$ | 20 |
| 4 | $NO_2$ | (cyclohexyl)—$N$—$CH_2$—$CH_3$ | 6 |
| 5 | $NO_2$ | $CH_2—CH_2—CH_2—N\underset{\diagdown\_\_\diagup}{\overset{\diagup\phantom{XX}\diagdown}{\phantom{XX}}}N—CH_3$ | 2 |
| 6 | $NO_2$ | $N(CH_3)_2$ | >100 |
| 7 | $NO_2$ | (N-piperidyl) | >100 |
| 8 | $NO_2$ | $CONH_2$ | >100 |
| 9 | $NH_2$ | $CH_2—CH_2—N(CH_3)_2$ | 2.5 |
| 10 | $NH_2$ | $CH_2—CH_2—N(CH_2—CH_3)_2$ | 3 |
| 11 | $NH_2$ | $CH_2—CH_2—N$(piperidino) | 1.5 |
| 12 | $NH_2$ | $CH_2—CH_2—N$(pyrrolidino) | 8 |
| 13 | $NH_2$ | $CH_2—CH_2—N\underset{\diagdown\_\_\diagup}{\overset{\diagup\phantom{XX}\diagdown}{\phantom{XX}}}O$ | 10 |
| 14 | $NH_2$ | $CH_2—CH_2—CH_2—N(CH_3)_2$ | 5 |
| 15 | $NH_2$ | $CH_2—CH_2—CH_2—N(CH_2—CH_3)_2$ | 25 |

-continued

| Ex. | X | Y | ID$_{50}$ |
|---|---|---|---|
| 16 | NH$_2$ | CH$_2$—CH$_2$—CH$_2$—N⟨piperazine⟩N—CH$_3$ | 10 |
| 17 | NH$_2$ | N(CH$_3$)$_2$ | 100 |
| 18 | Cl | CH$_2$—CH$_2$—N(CH$_3$)$_2$ | 0.8 |
| 19 | Cl | CH$_2$—CH$_2$—N⟨piperidine⟩ | 1.5 |
| 20 | Cl | CH$_2$—CH$_2$—N⟨hexamethyleneimine⟩ | 3.5 |
| 21 | Cl | CH$_2$—CH$_2$—N⟨morpholine⟩O | 100 |
| 22 | Cl | CH$_2$—CH$_2$—CH$_2$—N(CH$_3$)$_2$ | 2 |
| 23 | OH | CH$_2$—CH$_2$—N(CH$_3$)$_2$ | 3 |
| 24 | OH | CH$_2$—CH$_2$—N⟨piperidine⟩ | 3.5 |
| 25 | OH | CH$_2$—CH$_2$—N⟨morpholine⟩O | 100 |
| 26 | OCH$_3$ | CH$_2$—CH$_2$—N(CH$_3$)$_2$ | 1.5 |
| 27 | OCH$_3$ | CH$_2$—CH$_2$—N⟨piperidine⟩ | 0.75 |
| 28 | NHCO$_2$C$_2$H$_5$ | CH$_2$—CH$_2$—N(CH$_3$)$_2$ | 10 |
| 29 | NHCO$_2$C$_2$H$_5$ | CH$_2$—CH$_2$—N⟨piperidine⟩ | 10 |
| 30 | NHCOCH$_3$ | CH$_2$—CH$_2$—N(CH$_3$)$_2$ | 4 |
| 31 | NHCOCH$_3$ | CH$_2$—CH$_2$—N⟨piperidine⟩ | 5 |
| 32 | SO$_3$H | CH$_2$—CH$_2$—N⟨piperidine⟩ | >100 |
| 33 | C(CH$_3$)$_3$ | CH$_2$—CH$_2$—N(CH$_3$)$_2$ | 14 |

The embodiments of the invention in which an exclusive property or privilege is claimed are defined as follows:

1. A compound having the formula

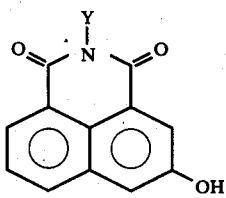

wherein Y is CH$_2$—CH$_2$N(CH$_3$)$_2$,

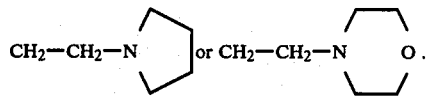

2. A compound having the formula

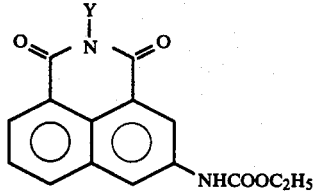

wherein Y is CH$_2$—CH$_2$—N(CH$_3$)$_2$ or

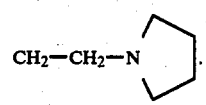

3. A compound having the formula

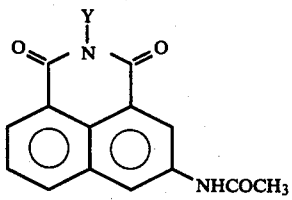

wherein Y is CH$_2$—CH$_2$—N(CH$_3$)$_2$ or

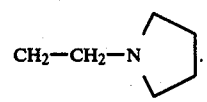

4. A compound having the formula

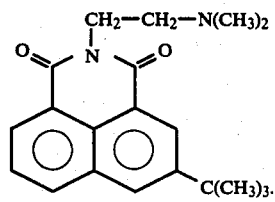

5. A compound having the formula

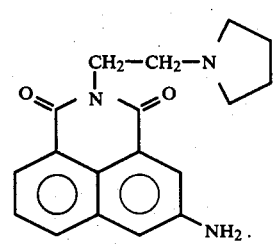

* * * * *